(12) United States Patent
Ben-Ezer

(10) Patent No.: US 8,477,309 B2
(45) Date of Patent: Jul. 2, 2013

(54) METHOD AND SYSTEM FOR INSPECTING BEVELED OBJECTS

(75) Inventor: Zehava Ben-Ezer, Moshav Balfuria (IL)

(73) Assignee: Camtek Ltd., Migdal Haemek (IL)

( * ) Notice: Subject to any disclaimer, the term of this patent is extended or adjusted under 35 U.S.C. 154(b) by 152 days.

(21) Appl. No.: 13/197,817

(22) Filed: Aug. 4, 2011

(65) Prior Publication Data

US 2012/0038921 A1  Feb. 16, 2012

Related U.S. Application Data

(60) Provisional application No. 61/372,242, filed on Aug. 10, 2010.

(51) Int. Cl.
*G01J 4/00* (2006.01)
*G01N 21/00* (2006.01)

(52) U.S. Cl.
USPC ..... 356/369; 356/364; 356/239.1; 356/239.2; 356/237.2

(58) Field of Classification Search
USPC .......... 356/364–369, 239.1, 237.2, 239.2
See application file for complete search history.

(56) References Cited

U.S. PATENT DOCUMENTS

| 5,483,346 | A | * | 1/1996 | Butzer | 356/369 |
| 7,193,711 | B2 | * | 3/2007 | Rassman et al. | 356/369 |
| 7,329,553 | B2 | * | 2/2008 | Yoon et al. | 438/29 |
| 7,973,838 | B2 | * | 7/2011 | McCutchen | 348/276 |
| 2008/0002202 | A1 | * | 1/2008 | Hall et al. | 356/369 |

* cited by examiner

*Primary Examiner* — Layla Lauchman
(74) *Attorney, Agent, or Firm* — Oren Reches

(57) ABSTRACT

An inspection system and a method. The method may include: illuminating the object with impinging light of a first polarization; performing a polarization based filtering of (a) multiple-reflected light signals, each multiple-reflected light signal being reflected from at least two different bevel side surfaces of the object, and (b) additional light signals, each additional light signal being reflected from a single element of the object, such as to suppress the multiple-reflected light signals, and to provide polarization based filtered light signals; and detecting the polarization based filtered light signals.

30 Claims, 11 Drawing Sheets

```
┌─────────────────────────────────────────────────────────────────────────────┐
│ Illuminating the object with impinging light of linear polarization along a first direction. │
│ The object includes a top surface and multiple beveled side surfaces. Each beveled side │
│    surfaces has a top edge that is directed along a beveled side surface direction. Each    │
│        beveled side surface direction is oriented in relation to the first direction. 1010        │
└─────────────────────────────────────────────────────────────────────────────┘
                                            │
                                            ▼
┌─────────────────────────────────────────────────────────────────────────────┐
│    Performing a polarization based filtering of multiple-reflected light signals and of     │
│ additional light signals such as to suppress the multiple-reflected light signals, to provide │
│ polarization based filtered light signals. The multiple-reflected light signals are reflected │
│ multiple times by multiple of beveled side surfaces of the multiple beveled side surfaces. │
│   The multiple-reflected light signals are of linear polarization along a second direction   │
│  that differs from the first direction. Each additional light signal is reflected from a single  │
│  element of the object. The additional light signals are of linear polarization along a third  │
│           direction that differs from the first direction and from the second direction. 1030           │
└─────────────────────────────────────────────────────────────────────────────┘
                                            │
                                            ▼
┌─────────────────────────────────────────────────────────────────────────────┐
│    Collecting the multiple-reflected light signals and collecting the additional light signals.    │
│                                          1040                                           │
└─────────────────────────────────────────────────────────────────────────────┘
                                            │
                                            ▼
┌─────────────────────────────────────────────────────────────────────────────┐
│                 Detecting the polarization based filtered light signals. 1050                  │
└─────────────────────────────────────────────────────────────────────────────┘
```

METHOD AND SYSTEM FOR INSPECTING BEVELED OBJECTS

RELATED APPLICATIONS

This application claims priority from U.S. provisional patent Ser. No. 61/372,242, filing date Aug. 10, 2010, which is incorporated herein by reference.

FIELD OF THE INVENTION

The invention relates to methods and systems for inspecting of objects and especially for suppressing glare.

BACKGROUND OF THE INVENTION

Various objects can be transparent and have a top surface and at least one other side surface that is bevel (hereinafter—beveled side surface).

These objects can be semiconductor devices, Light Emitting Diodes, etc. FIGS. 1 and 2 illustrates a prior object 10 that has a trapezoid cross section—it includes a horizontal bottom surface 13, a horizontal top surface 11, a first beveled side surface 12 and a second beveled side surface 14. The horizontal bottom surface 13 is smaller than the top surface 11. The first beveled side surface 12 is oriented at 45 degrees in relation to the horizon and the second beveled side surface 14 is oriented at minus 45 degrees (−45) in relation to the horizon.

FIG. 1 illustrates the object 10 as having multiple elements 15, although it may have elements of different sizes and shapes. These elements 15 are expected to be seen at an image of the object—one or more element can reflect light although the object 10 may have elements that are not reflective. The first beveled side surface 12 has a top edge 18 that is parallel to an imaginary Y-axis and the second beveled side surface 14 has a top edge 19 that is parallel to the imaginary Y-axis.

Top illumination (bright field illumination) may be reflected back from the top and bottom horizontal surfaces 11 and 13 of the object and from elements of the object, enabling inspecting them. This is illustrates in FIG. 3—arrows 22 and 21 are non-limiting examples of multiple-reflected light signals—light signals that are reflected multiple times by multiple of beveled side surfaces of the multiple beveled side surfaces.

Arrows 22 illustrate impinging light signals that are reflected from the first beveled side surface 12 towards the second beveled side surface 14 and from the second beveled side surface 14 towards a sensor.

Arrows 21 illustrate impinging light signals that are reflected from the second beveled side surface 14 towards the first beveled side surface 12 and from the first beveled side surface 12 towards a sensor.

The multiple-reflected light signals can cause a disturbance in an image of the object—as illustrated in FIG. 4. This disturbance can appear as a bright glare in an image of the object—as illustrated in grey areas 31 and 33 of image 30 of FIG. 4. The image 30 also includes images 35 of object elements 15 and a white background image portion 32 that corresponds to the bottom surface 13.

This disturbance may saturate specific zones (such as areas 31 and 33) in the image 30 and even if not, it is a disturbance in the image 30 that deteriorates or the inspection quality or prevents inspection at all.

There is a growing need to provide improved methods for inspecting objects while suppressing the bright glare.

SUMMARY

According to an embodiment of the invention a method may be provided and may includes illuminating the object with impinging light of a first polarization; performing a polarization based filtering of (a) multiple-reflected light signals, each multiple-reflected light signal being reflected from at least two different bevel side surfaces of the object, and (b) additional light signals, each additional light signal being reflected from a single element of the object, such as to suppress the multiple-reflected light signals, and to provide polarization based filtered light signals; and detecting the polarization based filtered light signals.

According to an embodiment of the invention an inspection system may be provided and may include (i) optics for illuminating the object with impinging light of a first polarization; performing a polarization based filtering of (a) multiple-reflected light signals, each multiple-reflected light signal being reflected from at least two different bevel side surfaces of the object, and (b) additional light signals, each additional light signal being reflected from a single element of the object, such as to suppress the multiple-reflected light signals, and to provide polarization based filtered light signals; and (ii) a sensor for detecting the polarization based filtered light signals.

According to an embodiment of the invention a method may be provided and may include: (a) illuminating the object with impinging light of linear polarization along a first direction. The object may include a top surface and multiple beveled side surfaces. Each beveled side surfaces has a top edge that may be directed along a beveled side surface direction. Each beveled side surface direction may be oriented in relation to the first direction; (b) performing a polarization based filtering of multiple-reflected light signals and of additional light signals such as to suppress the multiple-reflected light signals, to provide polarization based filtered light signals. The multiple-reflected light signals are reflected multiple times by multiple of beveled side surfaces of the multiple beveled side surfaces. The multiple-reflected light signals are of linear polarization along a second direction that differs from the first direction. Each additional light signal may be reflected from a single element of the object. The additional light signals are of linear polarization along a third direction that differs from the first direction and from the second direction; and (c) detecting the polarization based filtered light signals.

The performing of the polarization based filtering may include applying a filtering function that as to attenuate light signals that have a polarization that differs from a linear polarization along the third direction.

The second direction may be orthogonal to the third direction.

The first angle between at least one beveled side surface direction and the first direction substantially equals 45 degrees.

The polarization based filtering may be preceded by collecting the multiple-reflected light signals and collecting the additional light signals.

The illuminating of the object may be preceded by: polarizing input light by a linear polarization element to provide polarized light; directing the polarized light towards a non-polarizing beam splitter; and directing, by the non-polarizing beam splitter, the polarized light towards the object to provide the impinging light; and wherein the performing of the polarization based filtering may be preceded by collecting the additional light signals and the collecting of the multiple-reflected light signals by passing the additional light signals and the multiple-reflected light signals through the non-polarizing beam splitter.

The method may include spectral filtering at least one of the input light and the polarization based filtered light.

The illuminating of the object may be preceded by: directing input light towards a non-polarizing beam splitter; directing, by the non-polarizing beam splitter, the input light towards a linear polarization element; and polarizing the input light, by the linear polarization element to provide the impinging light. The performing a polarization based filtering may be executed by the linear polarization element.

The linear polarization element may be a closest optical element to the object.

The at least one optical components of collection optics may be positioned between the linear polarization element and the object. The collection optics may be for collecting the multiple-reflected light signals and the additional light signals.

The method may include detecting the polarization based filtered light signals by a sensor; and wherein the method further may include adjusting a polarization of the polarization based filtered light to a desired polarization of the sensor.

The desired polarization of the sensor may be a rotational polarization.

According to an embodiment of the invention an inspection system may be provided and may: (a) optics, arranged to: (i) illuminate an object with impinging light of linear polarization along a first direction. The object may include a top surface and multiple beveled side surfaces. Each beveled side surfaces has a top edge that may be directed along a beveled side surface direction. each beveled side surface direction may be oriented in relation to the first direction; (ii) perform a polarization based filtering of multiple-reflected light signals and of additional light signals such as to suppress the multiple-reflected light signals, to provide polarization based filtered light signals. The multiple-reflected light signals are reflected multiple times by multiple of beveled side surfaces of the multiple beveled side surfaces. The multiple-reflected light signals are of linear polarization along a third direction that differs from the first direction. Each additional light signal may be reflected from a single element of the object. The additional light signals are of linear polarization along a third direction that differs from the first direction and from the second direction; and (b) a sensor for detecting the polarization based filtered light signals.

The optics may include a first filtering element that may be arranged to perform the polarization based filtering by applying a filtering function that as to attenuate light signals that have a polarization that differs from a linear polarization along the second direction.

The second direction may be orthogonal to the third direction.

A first angle between at least one beveled side surface direction and the first direction may substantially equals 45 degrees.

The first filtering element may be preceded by at least one collecting optical component for collecting the multiple-reflected light signals and collecting the additional light signals.

the optics may include: a linear polarization element arranged to polarize input light to provide polarized light; a non-polarizing beam splitter arranged to receive the polarized light from the linear polarization element and to direct the polarized light towards the object to provide the impinging light; a first filtering element that may be arranged to perform the polarization based filtering; and a collecting optical component for collecting the multiple-reflected light signals and for collecting the additional light signals.

The collecting optical component may be positioned between the sensor and the first filtering element.

The collecting optical component may be positioned between the object and the first filtering element.

The inspection system may include at least one spectral filter arranged to perform spectral filtering of at least one of the input light and the polarization based filtered light.

The inspection system may include: a non-polarizing beam splitter arranged to receive input light; and a linear polarization element; wherein the non-polarizing beam splitter may be arranged to direct the input light towards the linear polarization element. The linear polarization element may be arranged to polarize the input light to provide the impinging light and to perform the polarization based filtering.

The linear polarization element may be a closest optical element to the object.

At least one optical components of the optics may be positioned between the linear polarization element and the object.

The inspection system may include a polarization adjustment element arranged to adjust a polarization of the polarization based filtered light to a desired polarization of the sensor.

The desired polarization of the sensor may be a rotational polarization.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

FIGS. 10-13 illustrate methods according to various embodiments of the invention.

DETAILED DESCRIPTION OF THE DRAWINGS

Figure 1:
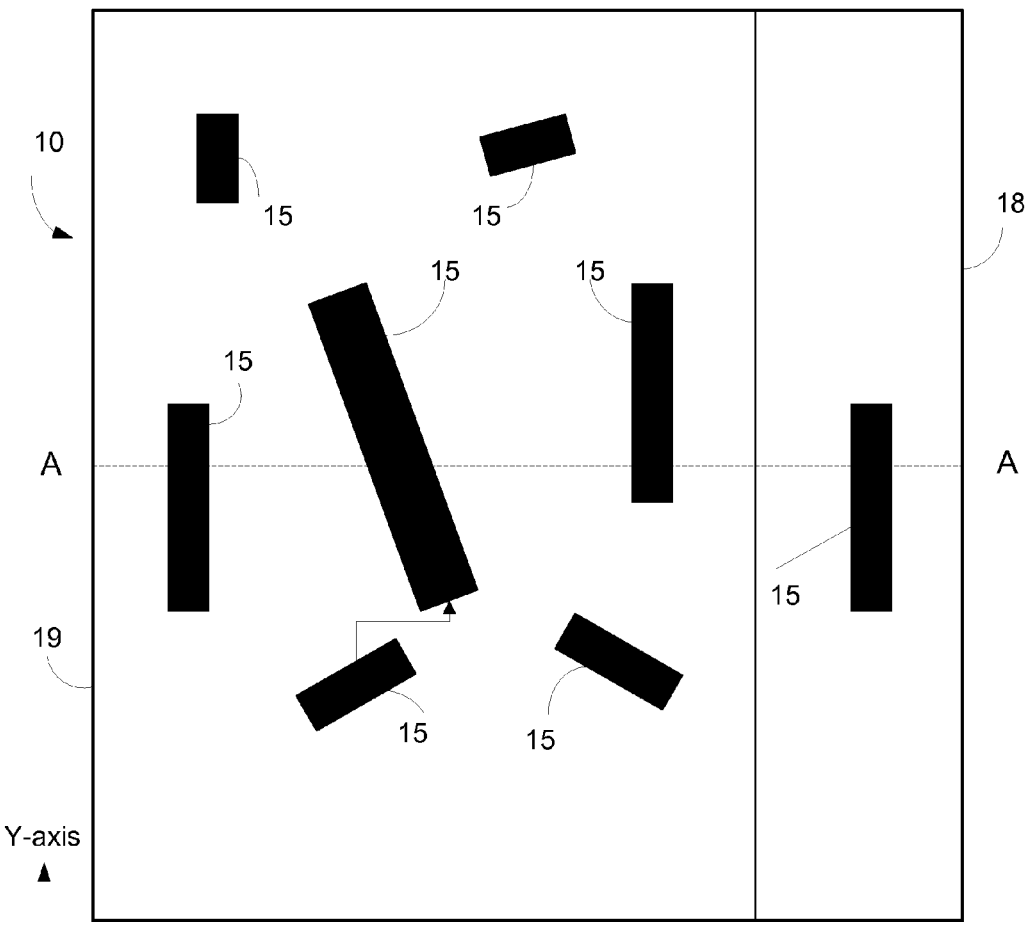
FIGS. 1 and 2 are a top view and a cross-sectional view of a prior art object 10.
Figure 2:
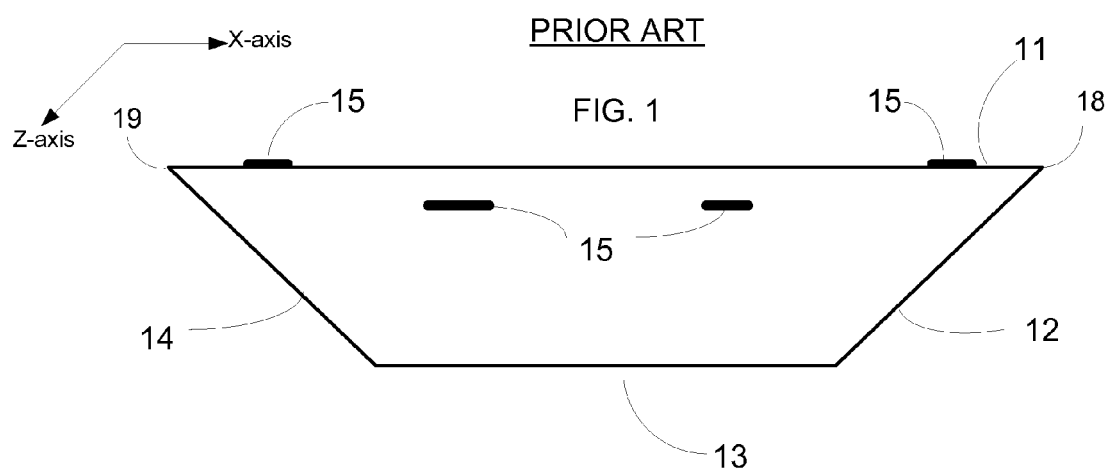

The foregoing and other objects, features, and advantages of the present invention will become more apparent from the following detailed description when taken in conjunction with the accompanying drawings. In the drawings, similar reference characters denote similar elements throughout the different views.

Because the illustrated embodiments of the present invention may for the most part, be implemented using electro-optical components and optic modules known to those skilled in the art, details will not be explained in any greater extent than that considered necessary for the understanding and appreciation of the underlying concepts of the present invention and in order not to obfuscate or distract from the teachings of the present invention.

The present invention can be practiced by employing conventional tools, methodology and components. Accordingly, the details of such tools, component and methodology are not set forth herein in detail. In the previous descriptions, numerous specific details are set forth, in order to provide a thorough understanding of the present invention. However, it should be recognized that the present invention might be practiced without resorting to the details specifically set forth.

For simplicity of explanation it is assumed that the object has an horizontal top surface, that the illumination includes normal illumination (optical axis of illumination is normal to the top surface of the object), that the collection includes normal collection (optical axis of collection is normal to the top surface of the object), and that the object includes two beveled side surfaces that are oriented by 45 degrees (and minus 45 degrees) to the horizon. It is noted that these assumptions are only an example and that the methods and systems illustrated in the specification can be applied mutatis mutandis to other illuminations and object configurations. It may be assumed that these assumptions provide maximal possible disturbances (maximal unwanted reflection towards the imaging module) but this is not necessarily so.

According to this invention, glare caused by reflection from beveled side surface can be reduced and even eliminated by polarized illumination and polarization based filtering. The polarization of impinging illumination may be linear and at direction of about forty five degrees to a direction of a top edge of a beveled side surface (this direction can be a bevel elongation direction and is illustrates as an x-axis in FIG. 5).

Figure 5:
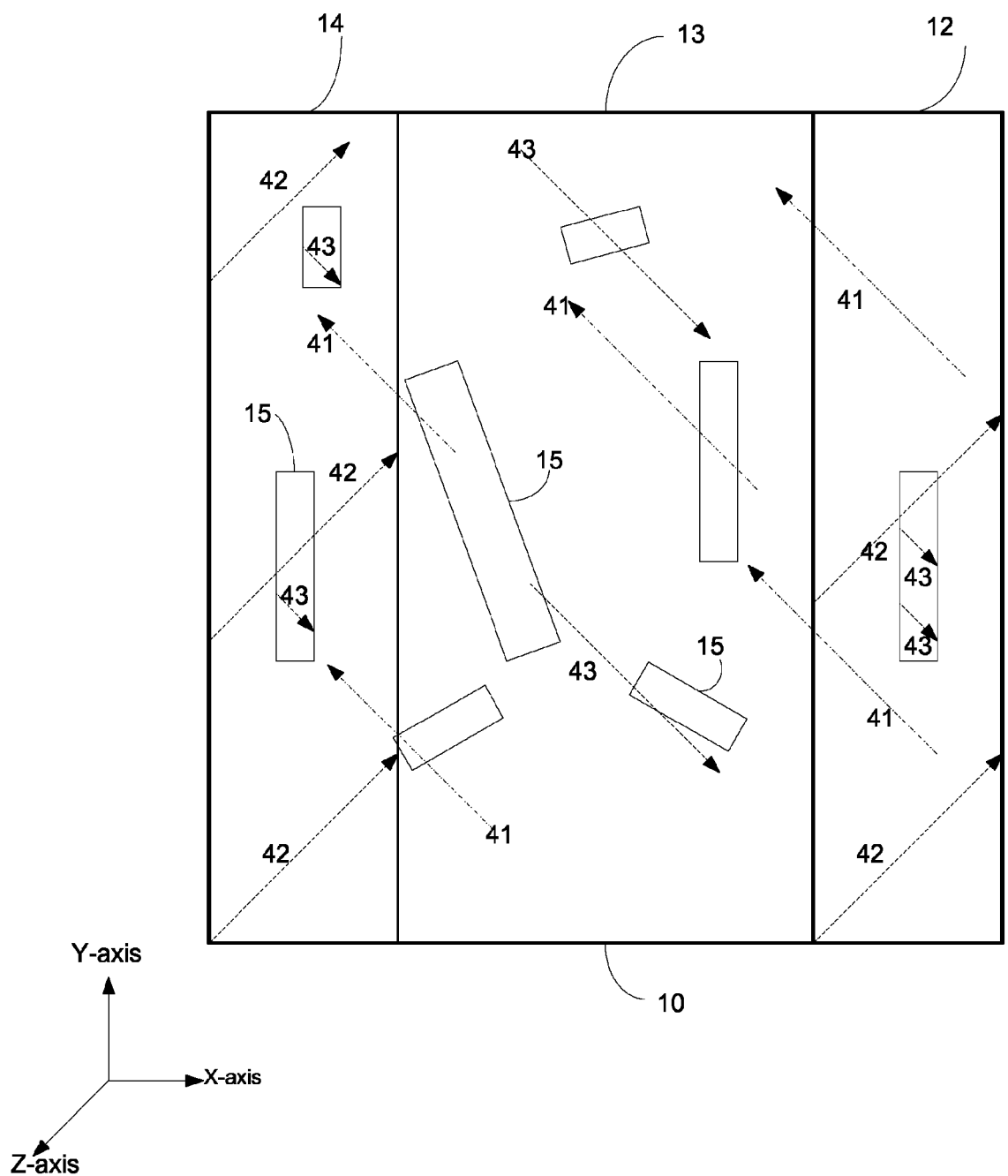
FIG. 5 illustrates various polarizations of multiple-reflected light signals and of additional light signals according to an embodiment of the invention.

FIG. 5 illustrates various polarizations of multiple-reflected light signals and of additional light signals according to an embodiment of the invention.

The impinging light is represented by arrows 41—it is of linear polarization along a first direction that is 135 degrees in relation to the imaginary x-axis.

Figure 3:
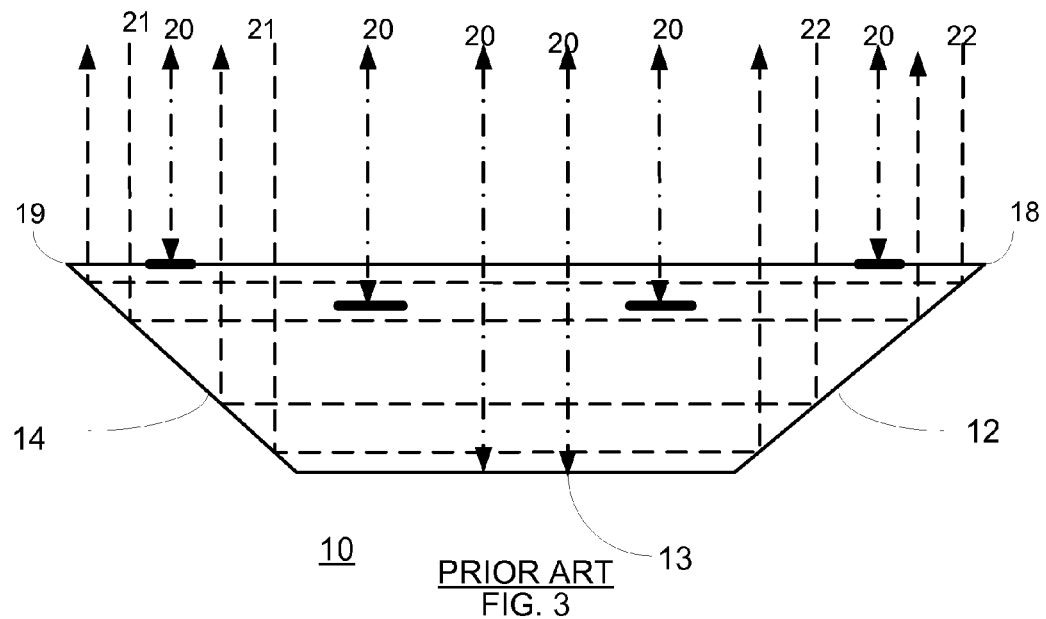
FIG. 3 is a prior art image of the object of FIG. 1.
Figure 4:
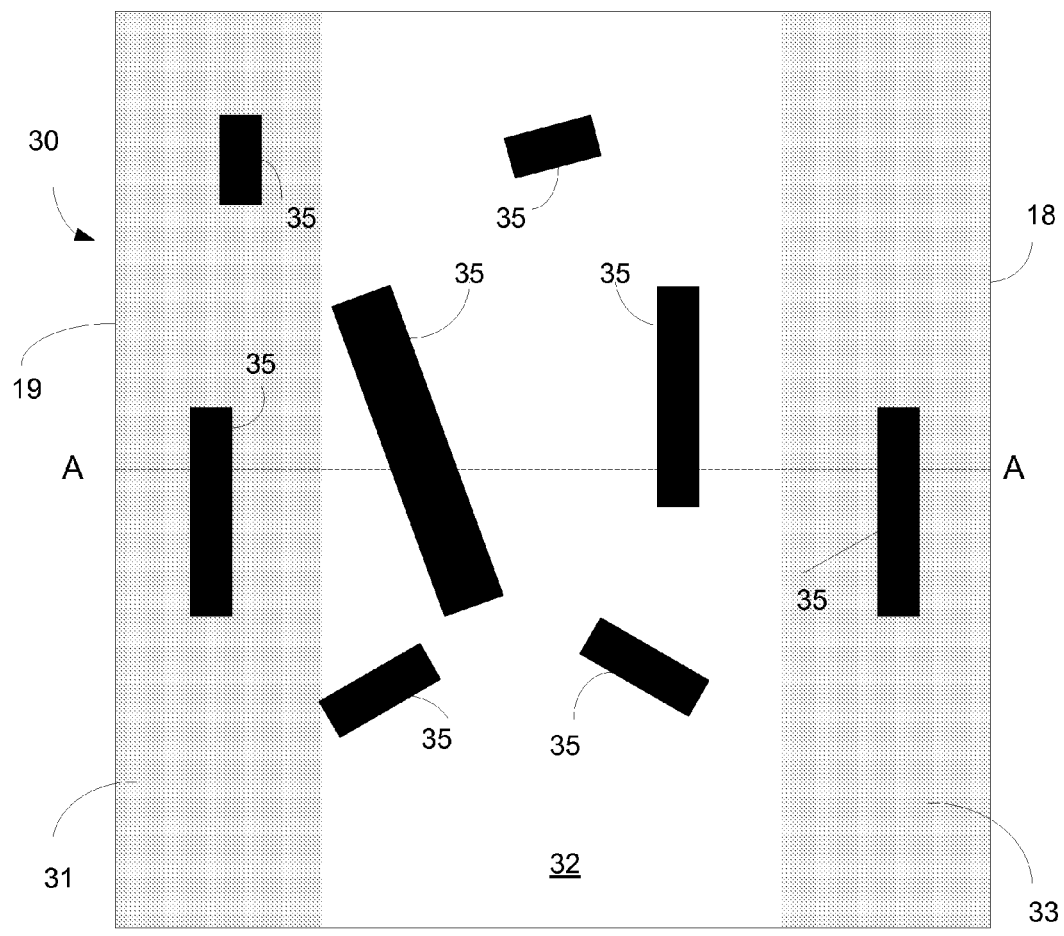
FIG. 4 illustrates multiple-reflected light signals and of additional light signals.

Multiple-reflected light signals (such as those denoted 21 and 22 in FIG. 3) are reflected from the object after their polarization is rotated by ninety degrees—their y-axis component of the polarization remains unchanged while their x-axis component of the polarization is rotated by one hundred and ninety degrees. The multiple-reflected light signals are of linear polarization having a second direction that is forty five degrees (45 degrees) in relation to the imaginary x-axis—as illustrated by arrows 42.

Additional light signals that are reflected once have their polarization rotated by one hundred and eighty degrees—are of linear polarization having a third direction that is minus forty five degrees (−45 degrees) in relation to the imaginary x-axis—as illustrated by arrows 43. These additional light signals appear in a zone that corresponds to the location of the bottom surface 13 of object 10.

Polarization based filtering can be applied, especially when the second direction 42 is orthogonal to the first and third directions. When the second and third directions are not normal to each other the filtering process can be less effective—the attenuation of the additional light signals (by the polarization based filtering) can increase and the attenuation of the multiple-reflected light signals (by the polarization based filtering) can decrease. Nevertheless, the polarization based filtering can be applied even at the latter case.

Figure 6:
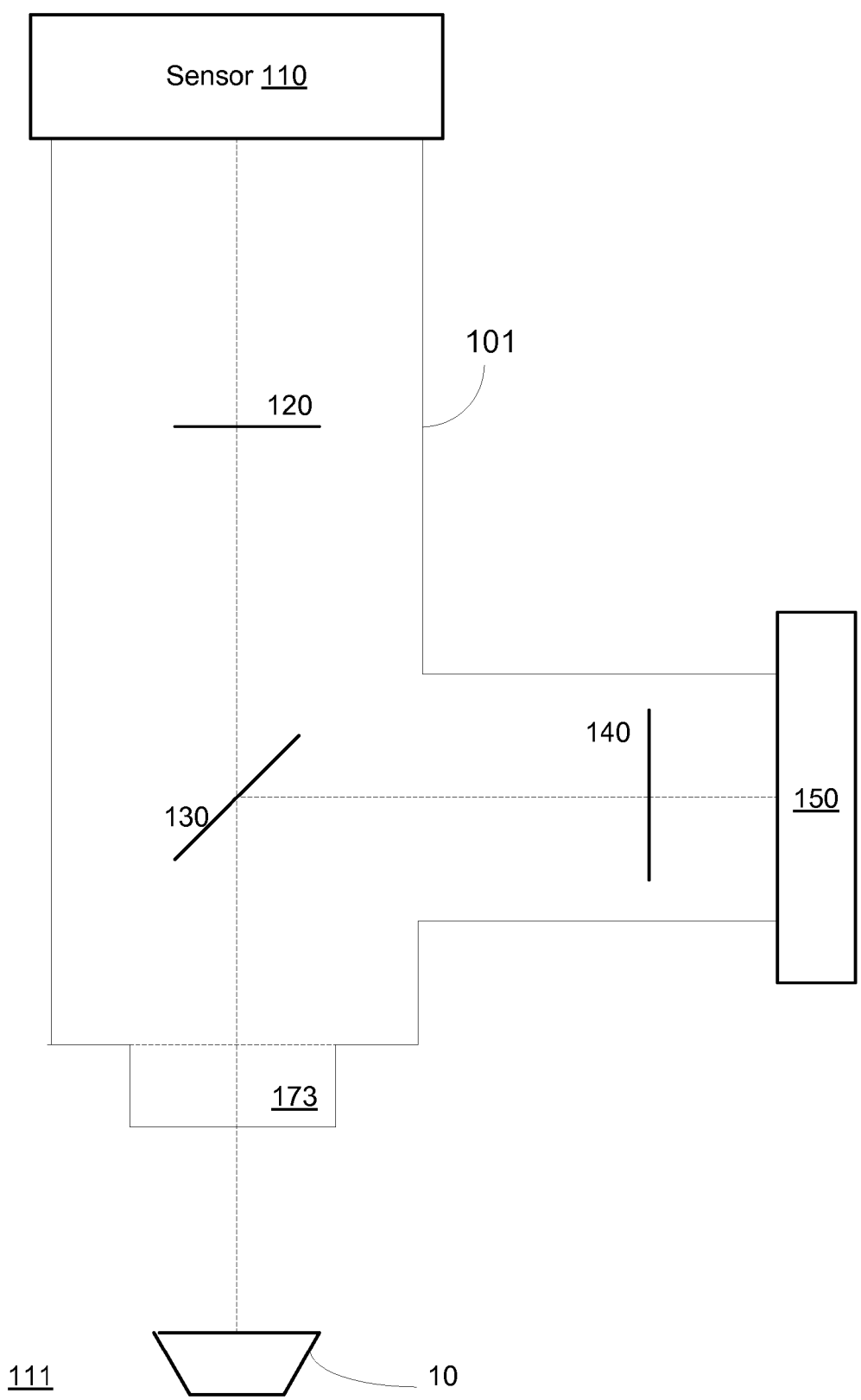
FIG. 6 illustrates a portion of a system according to an embodiment of the invention.

FIG. 6 illustrates a portion of system 111 according to an embodiment of the invention.

System 111 may include optics 101 and sensor 110. The sensor 110 can be a camera, an array of sensing elements and the like. System 111 may include additional components (not shown) such as a controller for controlling the system, an image processor for processing images acquires by sensor 110, a mechanical stage for supporting the object 10 and moving the object, and the like.

The object may include a top surface and multiple beveled side surfaces, each beveled side surfaces has a top edge that is directed along a beveled side surface direction, and each beveled side surface direction is oriented in relation to the first direction.

Optics 101 may include:
  a. A linear polarization element 140 arranged to polarize input light received from a non-polarized light source 150 to provide polarized light.
  b. A non-polarizing beam splitter 130 arranged to: (i) receive the polarized light from the linear polarization element 140 and to direct the polarized light towards the object 10 to provide impinging light; and (ii) transmit multiple-reflected light signals and additional light signals (from object 10) towards a first filtering element 120.
  c. A first filtering element 120 that is arranged to perform a polarization based filtering on the multiple-reflected light signals and additional light signals such as to attenuate (and even eliminate) the multiple-reflected light signals to provide polarization based filtered light signals. If, for example, the additional light signals are of linear polarization along the third direction and the multiple-reflected light signals are of linear polarization along a second direction (that differs from the third direction) then the first filtering element 120 can apply a filtering function that as to attenuate light signals that have a polarization that differs from a linear polarization along the second direction. The first filtering element 120 can be a linear polarization element.
  d. At least one collecting optical components such as lens 173 for collecting the multiple-reflected light signals and collecting the additional light signals. FIG. 6 illustrates lens 173 as being positioned between the object and the non-polarizing beam splitter 130. It is noted that the collecting optical components can be positioned between the non-polarizing beam splitter 130 and the first filtering element 120.

Figure 7:
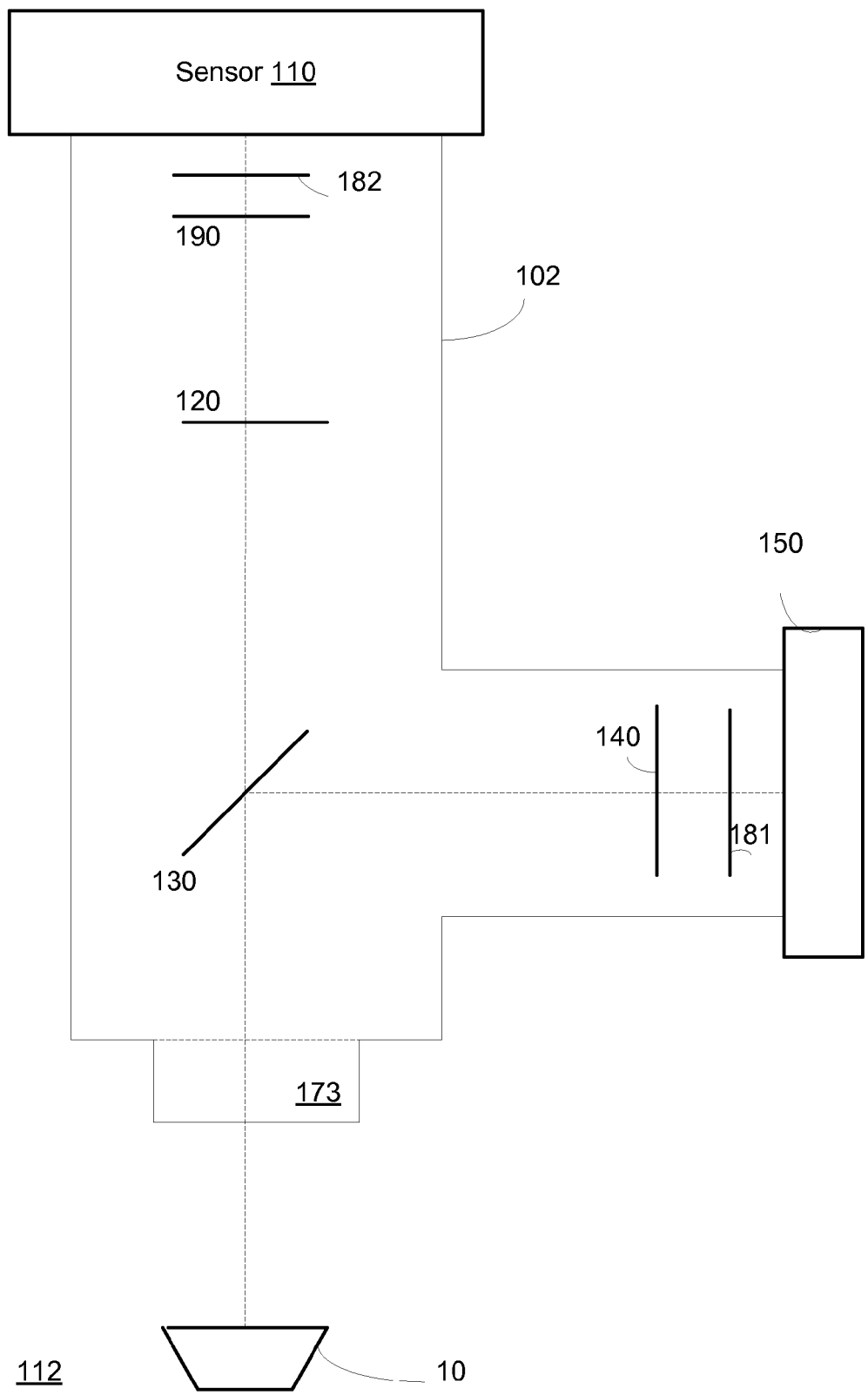
FIG. 7 illustrates a portion of a system according to an embodiment of the invention.

FIG. 7 illustrates a portion of system 112 according to an embodiment of the invention.

System 112 may include optics 102 and sensor 110. The sensor 110 can be a camera, an array of sensing elements and the like. System 112 may include additional components (not shown) such as a controller for controlling the system, an image processor for processing images acquires by sensor 110, a mechanical stage for supporting the object 10 and moving the object, and the like.

Optics 102 may include:
  a. A first spectral filter 181 arranged to perform a spectral filtering of input light received from a non-polarized light source 150 to provide spectral filtered input light.
  b. A linear polarization element 140 arranged to polarize the spectral filtered input light to provide polarized light.
  c. A non-polarizing beam splitter 130 arranged to: (i) receive the polarized light from the linear polarization element 140 and to direct the polarized light towards the object 10 to provide impinging light; and (ii) transmit multiple-reflected light signals and additional light signals (from object 10) towards a first filtering element 120.
  d. A first filtering element 120 that is arranged to perform a polarization based filtering on the multiple-reflected light signals and additional light signals such as to attenuate (and even eliminate) the multiple-reflected light signals. The first filtering element 120 outputs polarization based filtered signals. If, for example, the additional light signals are of linear polarization along the third direction and the multiple-reflected light signals are of linear polarization along a second direction (that differs from the third direction) then the first filtering element 120 can apply a filtering function that as to attenuate light signals that have a polarization that differs from a linear polarization along the second direction. The first filtering element 120 can be a linear polarization element.

e. Collecting optical components such as lens 173. FIG. 6 illustrates lens 173 as being positioned between the object and the non-polarizing beam splitter 130.

f. A polarization adjustment element 190 that is arranged to adjust a polarization of the polarization based filtered signals to a desired polarization of the sensor to provide polarization adjusted light signals. The polarization adjustment element 190 can be a quarter wave retarder arranged to convert a linear polarization of the polarization based filtered signals to circular polarized signals.

g. A second spectral filter 182 arranged to perform spectral filtering of polarization adjusted light signals to provide polarization adjusted and spectral filtered light signals to be sensed by sensor 110.

Optics 102 may include only a single spectral filter or more than two spectral filters. If optics 102 includes a plurality of spectral filters then the spectral filtering applied different spectral filters may be the same or may differ from each other. The order of components of optics 102 can differ from those illustrated in FIG. 7.

Figure 8:
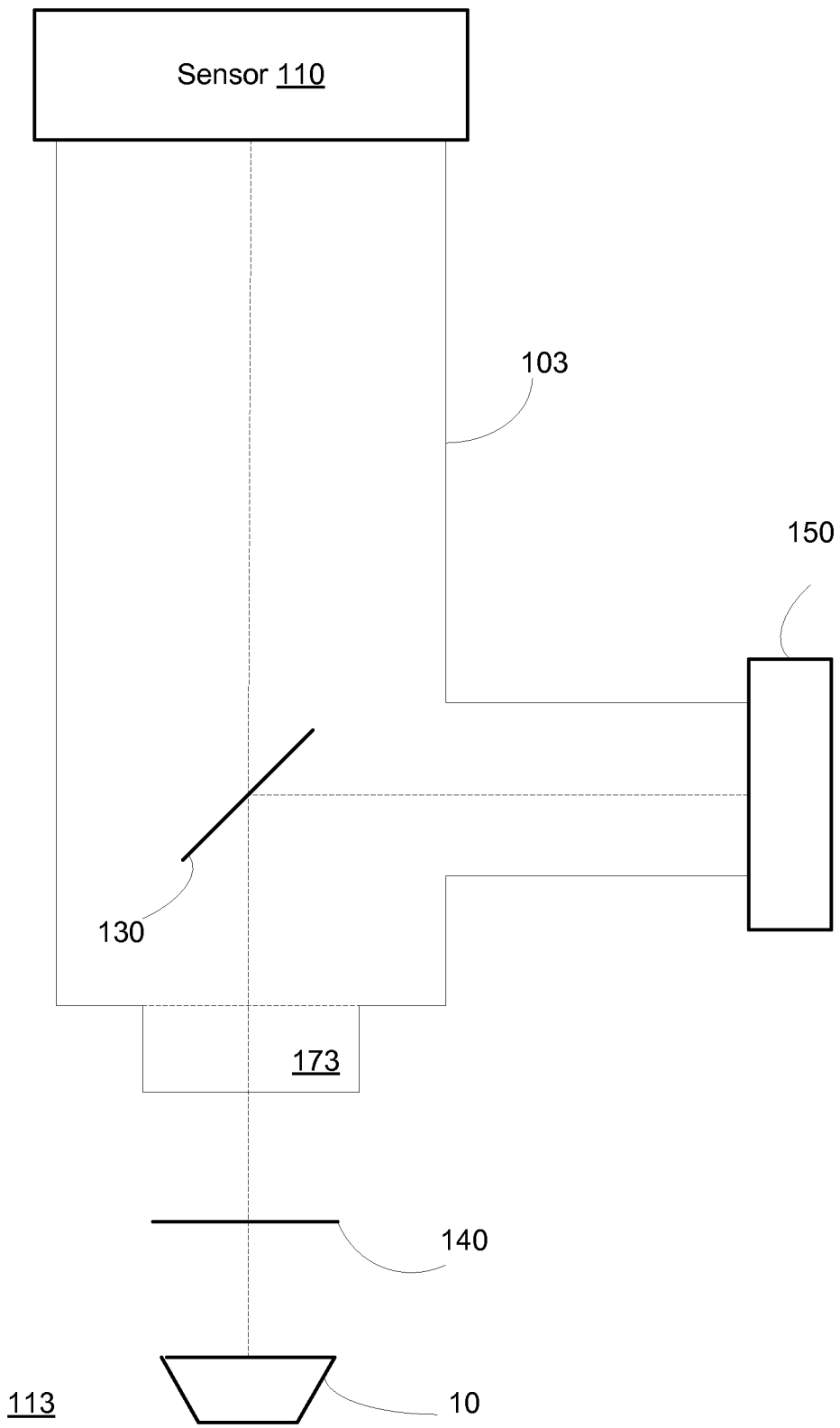
FIG. 8 illustrates a portion of a system according to an embodiment of the invention.
Figure 9:
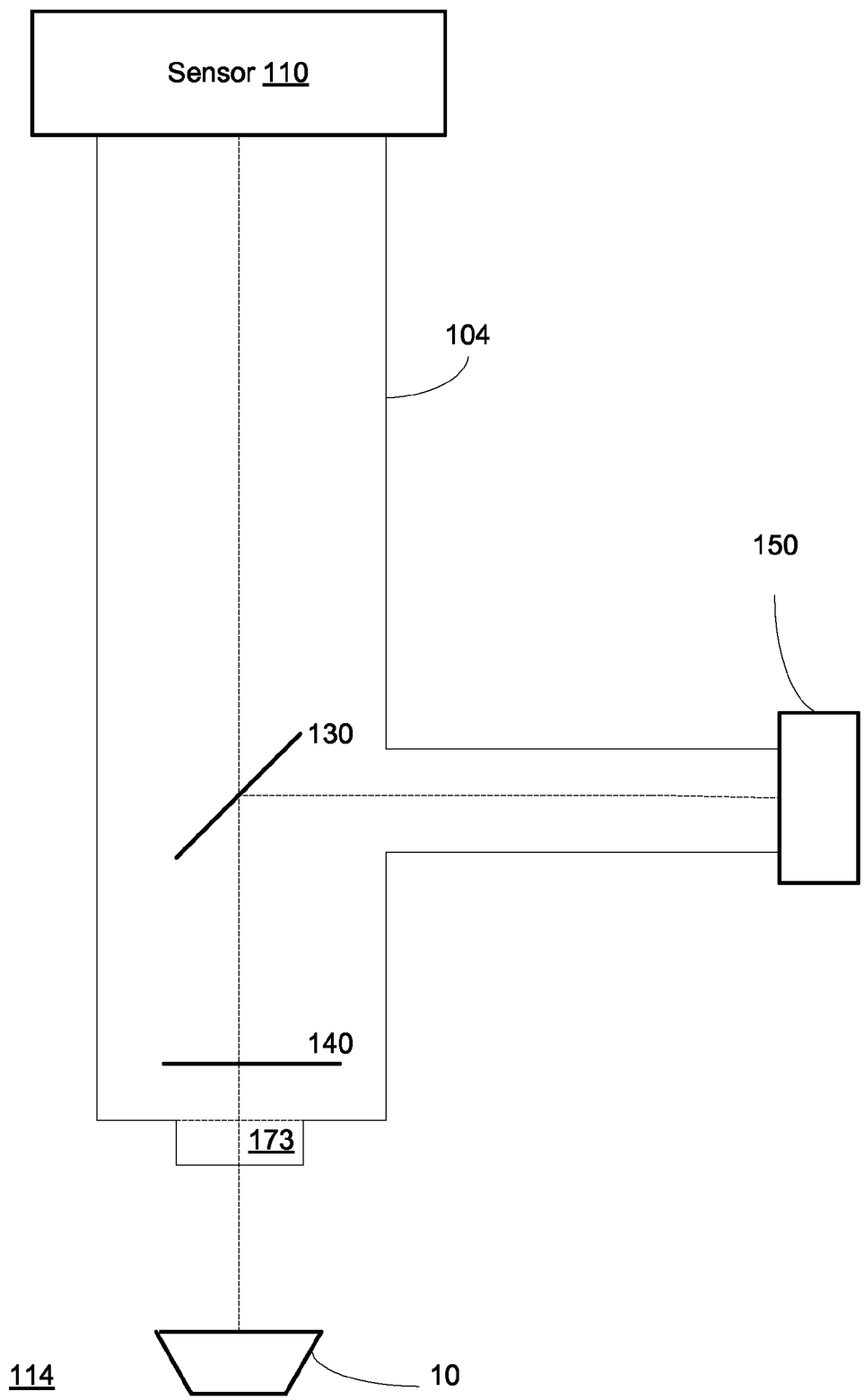
FIG. 9 illustrates a portion of a system according to an embodiment of the invention.

FIGS. 8 and 9 illustrate portions of system 113 and 114 according to various embodiments of the invention.

System 113 may include optics 103 and sensor 110. System 114 may include optics 103 and sensor 110. The sensor 110 can be a camera, an array of sensing elements and the like. Either one of systems 113 and 114 may include additional components (not shown) such as a controller for controlling the system, an image processor for processing images acquires by sensor 110, a mechanical stage for supporting the object 10 and moving the object, and the like.

Each one of optics 103 and 104 may include:

a. A non-polarizing beam splitter 130 arranged to: (i) receive non-polarized light from a non-polarize light source 150; (ii) direct the non-polarize light towards a linear polarizing element 140; (iii) transmit polarization based filtered signals from a linear polarization element 140 towards a collecting light component (such as lens 173) or towards sensor 110;

b. A linear polarization element 140 arranged to: (a) polarize the non-polarized light to provide polarized light that impinge onto the object 10; (b) perform a polarization based filtering on multiple-reflected light signals additional light signals received from the object such as to attenuate (and even eliminate) the multiple-reflected light signals to provide polarization based filtered light signals.

c. At least one collecting optical components such as lens 173 for providing a collection path that collects light.

FIG. 8 illustrates the linear polarization element 140 as being the closest component to the object 10 while FIG. 9 illustrates lens 173 as being positioned between the linear polarization element 140 and the object 10.

It is noted that any combinations of components from any of the illustrated above systems can be provided. For example, each system mentioned above can include one or more spectral filter, polarization adjustment element, multiple collection lenses, and the like. The order of components of each of the mentioned above systems, the amount of components per each of the mentioned above systems can change without departing from the spirit of the invention.

FIG. 10 illustrates method 1000, according to an embodiment of the invention. Method 1000 can be executed by any of the mentioned above systems.

Method 1000 starts by stage 1010 of illuminating the object with impinging light of linear polarization along a first direction. The object includes a top surface and multiple beveled side surfaces. Each beveled side surfaces has a top edge that is directed along a beveled side surface direction. Each beveled side surface direction is oriented in relation to the first direction.

Stage 1010 is followed by stage 1030 of performing a polarization based filtering of multiple-reflected light signals and of additional light signals such as to suppress the multiple-reflected light signals, to provide polarization based filtered light signals. The multiple-reflected light signals are reflected multiple times by multiple of beveled side surfaces of the multiple beveled side surfaces. The multiple-reflected light signals are of linear polarization along a second direction that differs from the first direction. Each additional light signal is reflected from a single element of the object. The additional light signals are of linear polarization along a third direction that differs from the first direction and from the second direction.

Stage 1030 may include applying a filtering function that as to attenuate light signals that have a polarization that differs from a linear polarization along the third direction.

The second direction may be orthogonal to the third direction.

A first angle between at least one beveled side surface direction and the first direction substantially equals 45 degrees.

Stage 1030 may be followed by stage 1040 of collecting the multiple-reflected light signals and collecting the additional light signals.

Stage 1040 is followed by stage 1050 of detecting the polarization based filtered light signals.

Figure 11:
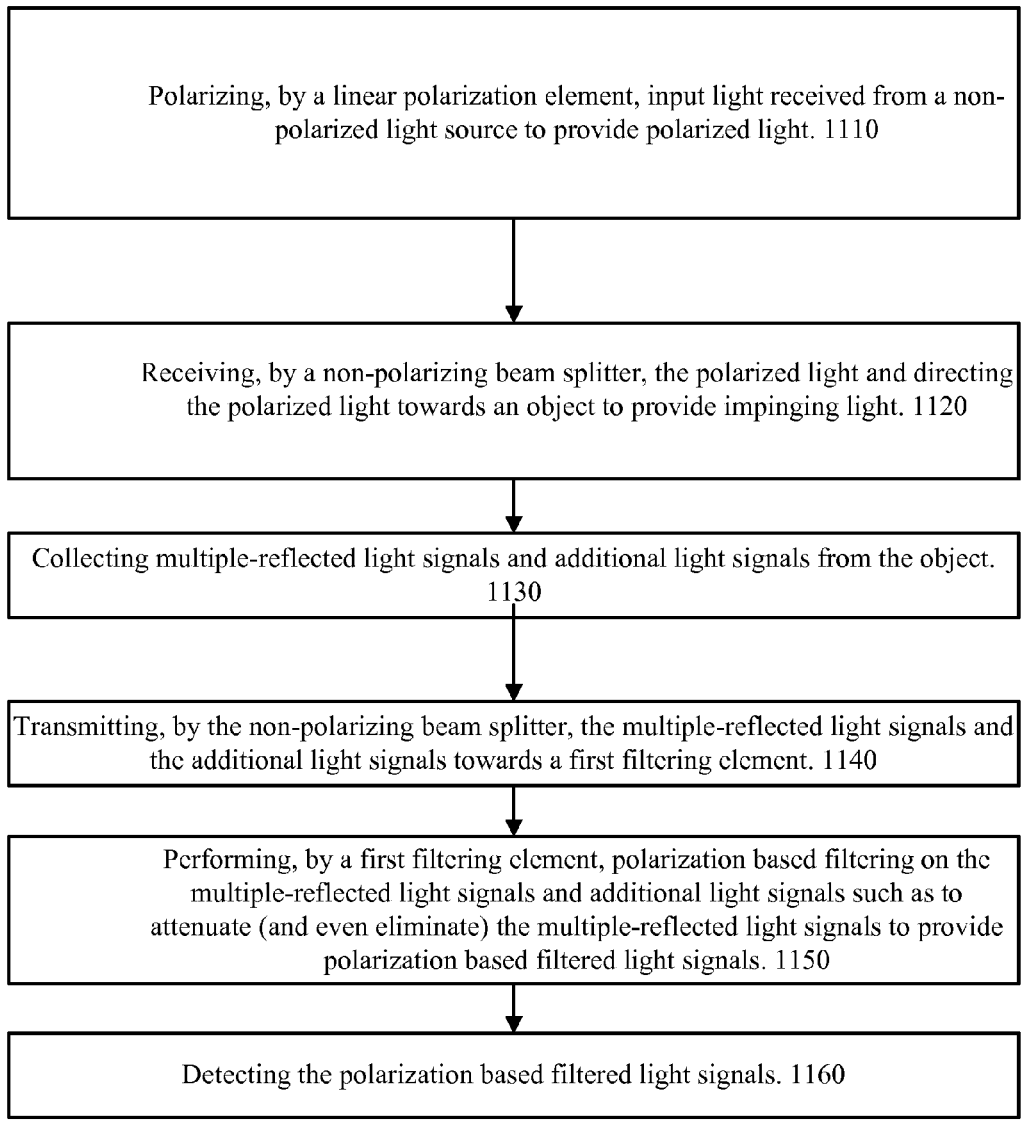

FIG. 11 illustrates method 1100 for inspecting an object, according to an embodiment of the invention. Method 1100 can be executed by system 111 of FIG. 6.

Method 1100 may include the following sequence of stages:

a. Stage 1110 of polarizing, by a linear polarization element, input light received from a non-polarized light source to provide polarized light.

b. Stage 1120 of receiving, by a non-polarizing beam splitter, the polarized light and directing the polarized light towards an object to provide impinging light.

c. Stage 1130 of collecting multiple-reflected light signals and additional light signals from the object.

d. Stage 1140 of transmitting, by the non-polarizing beam splitter, the multiple-reflected light signals and the additional light signals towards a first filtering element.

e. Stage 1150 of performing, by a first filtering element, polarization based filtering on the multiple-reflected light signals and additional light signals such as to attenuate (and even eliminate) the multiple-reflected light signals to provide polarization based filtered light signals.

f. Stage 1160 of detecting the polarization based filtered light signals.

Figure 12:
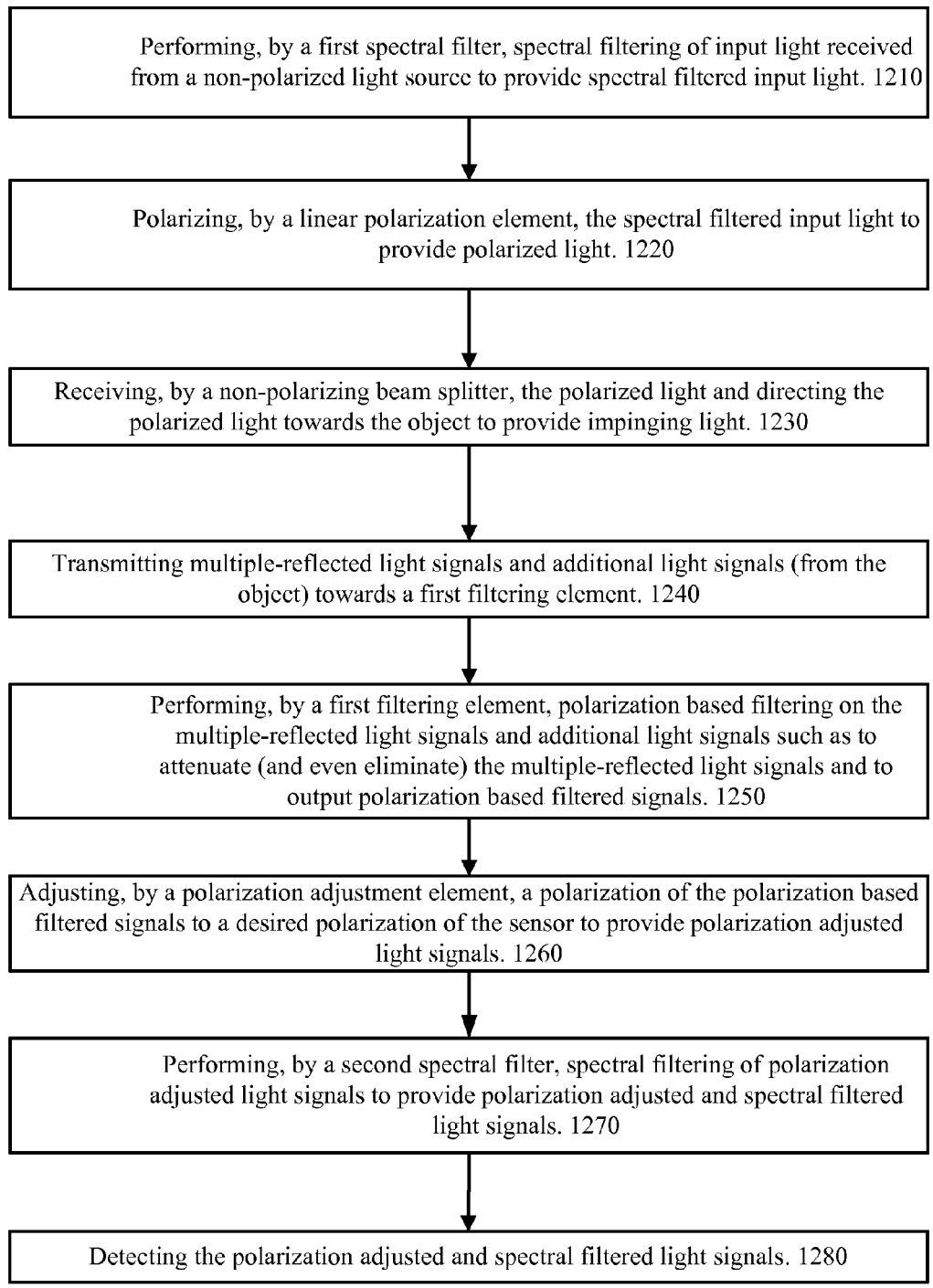

FIG. 12 illustrates method 1200 for inspecting an object, according to an embodiment of the invention. Method 1200 can be executed by system 112 of FIG. 7.

Method 1200 may include the following sequence of stages:

a. Stage 1210 of performing, by a first spectral filter, spectral filtering of input light received from a non-polarized light source to provide spectral filtered input light.

b. Stage 1220 of polarizing, by a linear polarization element, the spectral filtered input light to provide polarized light.

c. Stage 1230 of receiving, by a non-polarizing beam splitter, the polarized light and directing the polarized light towards the object to provide impinging light.

d. Stage 1240 of transmitting multiple-reflected light signals and additional light signals (from the object) towards a first filtering element.

e. Stage 1250 of performing, by a first filtering element, polarization based filtering on the multiple-reflected light signals and additional light signals such as to attenuate (and even eliminate) the multiple-reflected light signals and to output polarization based filtered signals.

f. Stage 1260 of adjusting, by a polarization adjustment element, a polarization of the polarization based filtered signals to a desired polarization of the sensor to provide polarization adjusted light signals.

g. Stage 1270 of performing, by a second spectral filter, spectral filtering of polarization adjusted light signals to provide polarization adjusted and spectral filtered light signals.

h. Stage 1280 of detecting the polarization adjusted and spectral filtered light signals.

Figure 13:
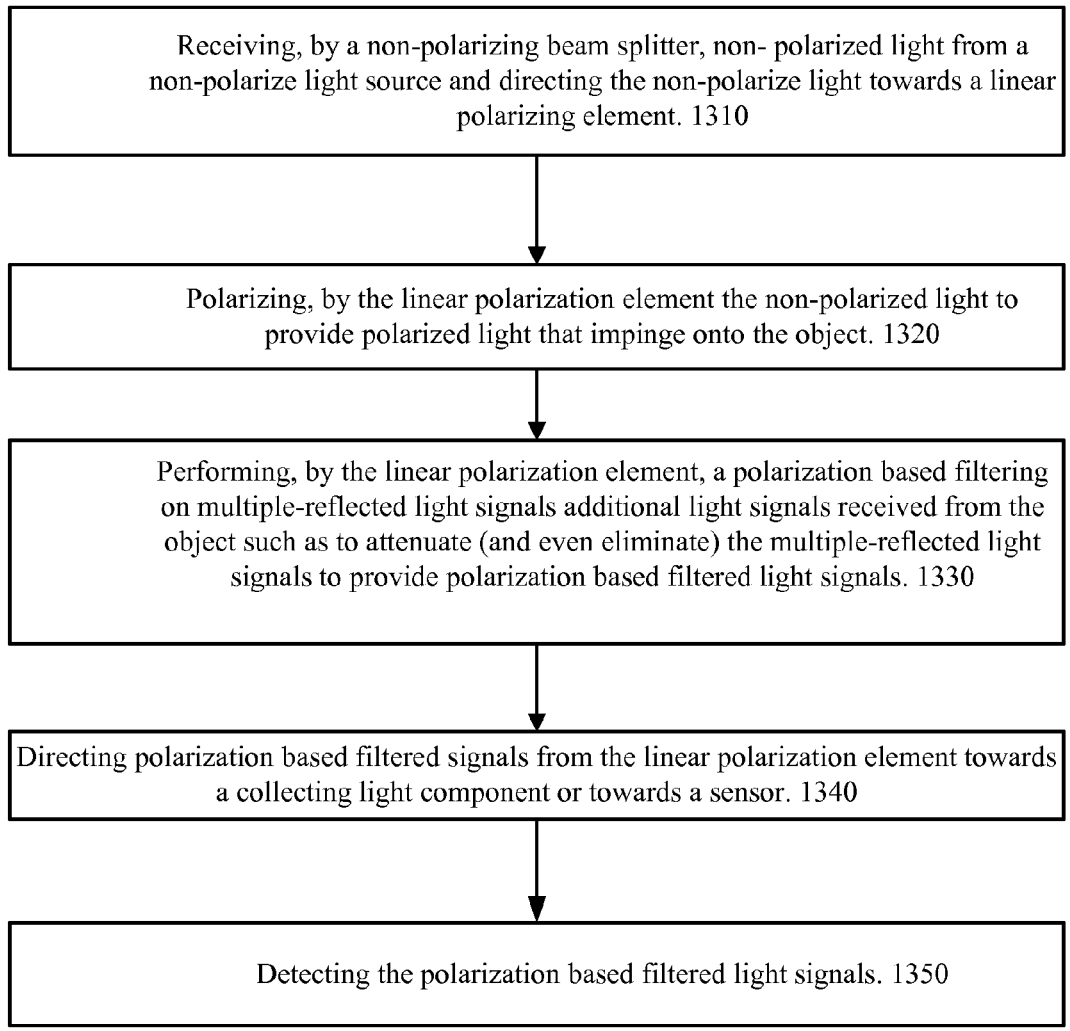

FIG. 13 illustrates method 1300 for inspecting an object, according to an embodiment of the invention. Method 1300 can be executed by systems 113 of 114 of FIG. 7 or 8.

Method 1300 may include the following sequence of stages:

a. Stage 1310 of receiving, by a non-polarizing beam splitter, non-polarized light from a non-polarize light source and directing the non-polarize light towards a linear polarizing element.

b. Stage 1320 of polarizing, by the linear polarization element the non-polarized light to provide polarized light that impinge onto the object;

c. Stage 1330 of performing, by the linear polarization element, a polarization based filtering on multiple-reflected light signals additional light signals received from the object such as to attenuate (and even eliminate) the multiple-reflected light signals to provide polarization based filtered light signals;

d. Stage 1340 of directing polarization based filtered signals from the linear polarization element towards a collecting light component or towards sensor 110;

e. Stage 1350 of detecting the polarization based filtered light signals.

Any combination of any stages of any of the mentioned above methods can be provided.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

I claim:

1. A method, comprising:
    illuminating the object with impinging light of a first polarization;
    performing a polarization based filtering of (a) multiple-reflected light signals, each multiple-reflected light signal being reflected from at least two different bevel side surfaces of the object, and (b) additional light signals, each additional light signal being reflected from a single element of the object, such as to suppress the multiple-reflected light signals, and to provide polarization based filtered light signals; and
    detecting the polarization based filtered light signals.

2. The method according to claim 1, wherein the first polarization is a linear polarization along a first direction; wherein the multiple-reflected light signals are of linear polarization along a second direction that differs from the first direction; and wherein the additional light signals are of linear polarization along a third direction that differs from the first direction and from the second direction.

3. The method according to claim 2, wherein the performing of the polarization based filtering comprises applying a filtering function to attenuate light signals that have a polarization that differs from a linear polarization along the third direction.

4. The method according to claim 2, wherein the second direction is orthogonal to the third direction.

5. The method according to claim 1, wherein the object comprise a top surface and multiple beveled side surfaces; wherein at least one beveled side surface has a top edge that is directed along a beveled side surface direction; and wherein a first angle between at least one beveled side surface direction and the first direction substantially equals 45 degrees.

6. The method according to claim 1, wherein the polarization based filtering is preceded by collecting the multiple-reflected light signals and collecting the additional light signals.

7. The method according to claim 1, wherein the illuminating of the object is preceded by:
    polarizing input light by a linear polarization element to provide polarized light;
    directing the polarized light towards a non-polarizing beam splitter; and directing, by the non-polarizing beam splitter, the polarized light towards the object to provide the impinging light; and
    wherein the performing of the polarization based filtering is preceded by collecting the additional light signals and the collecting of the multiple-reflected light signals by passing the additional light signals and the multiple-reflected light signals through the non-polarizing beam splitter.

8. The method according to claim 6, further comprising spectral filtering at least one of the input light and the polarization based filtered light.

9. The method according to claim 1, wherein the illuminating of the object is preceded by:
    directing input light towards a non-polarizing beam splitter;
    directing, by the non-polarizing beam splitter, the input light towards a linear polarization element; and
    polarizing the input light, by the linear polarization element to provide the impinging light;
    wherein the performing a polarization based filtering is executed by the linear polarization element.

10. The method according to claim 8, wherein the linear polarization element is a closest optical element to the object.

11. The method according to claim 8, wherein at least one optical component of collection optics is positioned between the linear polarization element and the object; wherein the collection optics is for collecting the multiple-reflected light signals and the additional light signals.

12. The method according to claim 1, comprising detecting the polarization based filtered light signals by a sensor; and wherein the method further comprising adjusting a polarization of the polarization based filtered light to a desired polarization of the sensor.

13. The method according to claim 11, wherein the desired polarization of the sensor is a rotational polarization.

14. The method according to claim 1, wherein each beveled side surfaces has a top edge that is directed along a beveled side surface direction; wherein each beveled side surface direction is oriented in relation to the first direction.

15. An inspection system, comprising:
optics, arranged to:
illuminate the object with impinging light of a first polarization; and
perform a polarization based filtering of (a) multiple-reflected light signals, each multiple-reflected light signal being reflected from at least two different bevel side surfaces of the object, and (b) additional light signals, each additional light signal being reflected from a single element of the object, such as to suppress the multiple-reflected light signals, and to provide polarization based filtered light signals; and
a sensor for detecting the polarization based filtered light signals.

16. The inspection system according to claim 15, wherein the first polarization is a linear polarization along a first direction; wherein the multiple-reflected light signals are of linear polarization along a second direction that differs from the first direction; and wherein the additional light signals are of linear polarization along a third direction that differs from the first direction and from the second direction.

17. The inspection system according to claim 16, wherein the performing of the polarization based filtering comprises applying a filtering function to attenuate light signals that have a polarization that differs from a linear polarization along the third direction.

18. The inspection system according to claim 16, wherein the second direction is orthogonal to the third direction.

19. The inspection system according to claim 16, wherein the object comprise a top surface and multiple beveled side surfaces; wherein at least one beveled side surface has a top edge that is directed along a beveled side surface direction; and wherein a first angle between at least one beveled side surface direction and the first direction substantially equals 45 degrees.

20. The inspection system according to claim 15, wherein the first filtering element is preceded by at least one collecting optical component for collecting the multiple-reflected light signals and collecting the additional light signals.

21. The inspection system according to claim 15, wherein the optics comprises:
a linear polarization element arranged to polarize input light to provide polarized light;
a non-polarizing beam splitter arranged to receive the polarized light from the linear polarization element and to direct the polarized light towards the object to provide the impinging light;
a first filtering element that is arranged to perform the polarization based filtering; and
a collecting optical component for collecting the multiple-reflected light signals and for collecting the additional light signals.

22. The inspection system according to claim 21, wherein the collecting optical component is positioned between the sensor and the first filtering element.

23. The inspection system according to claim 21, wherein the collecting optical component is positioned between the object and the first filtering element.

24. The inspection system according to claim 15, comprising at least one spectral filter arranged to perform spectral filtering of at least one of the input light and the polarization based filtered light.

25. The inspection system according to claim 15, comprising:
a non-polarizing beam splitter arranged to receive input light; and
a linear polarization element;
wherein the non-polarizing beam splitter is arranged to direct the input light towards the linear polarization element;
wherein the linear polarization element is arranged to polarize the input light to provide the impinging light and to perform the polarization based filtering.

26. The inspection system according to claim 25, wherein the linear polarization element is a closest optical element to the object.

27. The inspection system according to claim 25, wherein at least one optical components of the optics is positioned between the linear polarization element and the object.

28. The inspection system according to claim 15, comprising a polarization adjustment element arranged to adjust a polarization of the polarization based filtered light to a desired polarization of the sensor.

29. The inspection system according to claim 28, wherein the desired polarization of the sensor is a rotational polarization.

30. The inspection system according to claim 15, wherein each beveled side surfaces has a top edge that is directed along a beveled side surface direction; wherein each beveled side surface direction is oriented in relation to the first direction.

* * * * *